United States Patent [19]

Föry et al.

[11] 4,053,496

[45] Oct. 11, 1977

[54] PRODUCTS FROM THE HYDROLYSIS OF β-HALOGENOETHYL-SILANES AND THEIR USE AS AGENTS FOR THE REGULATION OF PLANT GROWTH

[75] Inventors: Werner Föry, Basel; Hanspeter Fischer, Bottmingen; Dieter Lohmann, Pratteln; Gerd Greber, Binningen, all of Switzerland

[73] Assignee: Ciba-Geigy Corporation, Ardsley, N.Y.

[21] Appl. No.: 647,484

[22] Filed: Jan. 8, 1976

Related U.S. Application Data

[63] Continuation of Ser. No. 415,081, Nov. 12, 1973, abandoned.

[30] Foreign Application Priority Data

Nov. 15, 1972 Switzerland .................... 16601/72

[51] Int. Cl.$^2$ ............................ C07F 7/04; C07F 7/18

[52] U.S. Cl. ................................. 260/448.8 R; 71/79
[58] Field of Search .................................. 260/448.8 R

[56] References Cited

U.S. PATENT DOCUMENTS 3,928,906   12/1975   Leeper et al. ................. 260/448.8 R

*Primary Examiner*—Paul F. Shaver
*Attorney, Agent, or Firm*—Harry Falber

[57] ABSTRACT

The present invention relates to partially polymerized products obtained by hydrolysis of β-halogenoethylsilanes and to the hydrolysis of the said monomeric silanes with water or an aqueous medium. The dimers are the preferred final products. The invention is further concerned with agents and methods for the regulation and control of plant development, especially for promoting fruit abcission as well as resin and latex flow in trees, using the said partially polymerized β-halogeno silane hydrolysates as the active ingredients.

7 Claims, No Drawings

PRODUCTS FROM THE HYDROLYSIS OF β-HALOGENOETHYL-SILANES AND THEIR USE AS AGENTS FOR THE REGULATION OF PLANT GROWTH

This is a continuation of application Ser. No. 415,081 filed on Nov. 12, 1973 now abandoned.

The present invention relates to products obtained from the hydrolysis of β-halogenoethyl-silanes, as well as to agents and processes for the regulation and control of plant growth in order to improve the yield, and facilitate the harvesting, of agricultural, forestry and gardening products by application of higher molecular products from the hydrolysis of β-halogenoethyl-silanes, and also to processes for the preparation of these products of hydrolysis.

It has been found that the agents and their active substances according to the present invention have a surprisingly favourable action on the growth and on the differentiation of plant parts and plant tissues above and below the surface of the soil. THe new agents and their active substances are in many respects superior to the 2-halogenoethyl-silane-monomers known from DOS No. 2,149,680 and from the Belgian Pat. No. 773,491, and to other 2-halogenoethyl-silane-monomers, which are similar active substances with regard to their mode of acting, and they thus constitute a valuable contribution to the art.

The active substances contained in the new agents are higher molecular, partially polymerised products of hydrolysis, with a degree of polymerisation of at most 3, of monomeric β-halogenoethyl-silanes of the formula

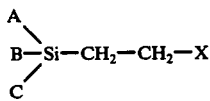

(I)

wherein

X represents chlorine or bromine,

A represents a radical $-S-R_1$, $-N\begin{subarray}{l}R_2\\R_3\end{subarray}$, $-O-R_4$, phenyl, chlorine or a lower alkyl radical such as methyl, B represents a radical $-S-R_5$, $N\begin{subarray}{l}R_2\\R_3\end{subarray}$, $-O-R_6$, phenyl, chlorine or a lower alkyl radical such as methyl, and C represents a radical $-S-R_7$, $-N\begin{subarray}{l}R_2\\R_3\end{subarray}$, $$-O-\underset{\underset{B}{|}}{\overset{\overset{A}{|}}{Si}}-CH_2-CH_2-X,$$

$$\left(-O-\underset{\underset{B}{|}}{\overset{\overset{A}{|}}{Si}}-O-\right)_n, \text{ wherein n is an integer up to 5,}$$

also a radical $-O-R_8$, phenyl, $-OH$, chlorine or a lower alkyl radical such as methyl.

The symbols $R_1$, $R_5$ and $R_7$ each independently represent alkyl radicals; alkyl radicals substituted by alkoxy, alkylthio, alkoxycarbonyl, phenyl, cycloalkyl or heterocyclic radicals; as well as alkenyl, alkynyl, cycloalkyl and cycloalkenyl radicals; phenyl radicals optionally mono- or polysubstituted by alkyl, alkoxy, alkylthio and/or halogen or benzyl radicals optionally mono- or polysubstituted by alkyl, alkoxy, alkylthio and/or halogen.

$R_3$ represents alkyl which can be substituted by alkoxy, alkylthio, phenyl, cycloalkyl, or by a heterocyclic radical; also cycloalkyl; cycloalkenyl; alkenyl; alkynyl; phenyl optionally mono- or polysubstituted by alkyl, alkoxy, alkylthio and/or halogen; or benzyl optionally mono- or polysubstituted by alkyl, alkoxy, alkylthio and/or halogen.

$R_2$ represents hydrogen or the same as $R_3$, whereby, however, $R_2$ and $R_3$ together with the adjacent nitrogen atom can also from a saturated or unsaturated ring system.

$R_4$, $R_6$ and $R_8$ each independently represent alkyl radicals; alkyl radicals substituted by halogen, alkoxy, alkenyloxy, phenoxy, cycloalkyl, alkylthio, alkoxycarbonyl, by a heterocyclic radical and/or by di- and trialkylammonio; alkenyl; cycloalkenyl; alkenyl, alkynyl or cycloalkyl substituted by phenyl, substituted phenyl or halogen; phenyl radicals optionally mono- or polysubstituted by cyano, nitro, alkyl, halogenoalkyl, alkoxy, alkylthio, alkanoyl and/or alkoxycarbonyl; or benzyl radicals mono- or polysubstituted by alkyl, alkoxy and/or halogen.

By lower alkyl radicals are meant straight-chain or branched radicals having 1 to 6 carbon atoms. One, two or three of the symbols $R_4$, $R_6$ and $R_8$ can also represent the group $-COR_9$ wherein $R_9$ stands for an alkyl, alkenyl or alkynyl radical, a halogenoalkyl or halogenoalkenyl radical, an alkyl or alkenyl radical substituted by alkoxy, alkylthio, cycloalkyl or phenyl, whereby phenyl can be substituted by alkyl, alkoxy and/or halogen, also for an alkoxyalkyl radical, an alkoxycarbonylalkyl radical, a benzoylalkyl radical, or a phenyl radical that can be optionally substituted by halogen, lower alkyl or alkoxy, and, finally, for a 5- or 6-membered heterocyclic radical.

$R_4$, $R_6$ and $R_8$, also as $-COR_9$ can form, together with the adjacent atoms, a silicon-containing, saturated or unsaturated heterocyclic ring system.

Alkyl radicals are in each case straight-chain or branched radicals having 1 to 18 carbon atoms, such as, e.g. methyl, ethyl, n-propyl, isopropyl, n-butyl, sec-butyl, n-hexyl, n-octyl, n-dodecyl, n-octadecyl, etc.. The straight-chain and branched alkyl radicals having 1 to 8 carbon atoms are particularly preferred, and form also the alkyl moiety of alkoxy, alkylthio, di- and trialkylammonio or alkoxycarbonyl substituents of an alkyl radical or of a phenyl radical. In the case of halogenoalkyl radicals, these are alkyl radicals having 1 to 6 carbon atoms, which can be substituted by fluorine, chlorine and/or bromine, such as, e.g. trifluoromethyl, 2-chloroethyl, 6-chlorohexyl, etc.. By alkenyl radicals in formula I are meant straight-chain or branched radicals having 3 to 18 carbon atoms, e.g. propenyl, butenyl, octenyl, decenyl or heptadecenyl radicals. These alkenyl radicals can be mono- or polysubstituted by halogen such as fluorine, chlorine, bromine and/or iodine, or by phenyl. Alkenyl radicals having 3 to 6 carbon atoms form the alkenyl part of alkenyloxy radicals. Alkynyl radicals preferably contain 3 to 8 carbon atoms in a straight chain, such as, e.g. 2-propinyl, 2-butinyl or 3-hexinyl. By cycloaliphatic radicals are meant mono- or polycyclic cycloalkyl or cycloalkenyl radicals having 3 to 12 carbon atoms, such as, e.g. cyclopropyl, cyclopentyl, cyclopentenyl, cyclohexenyl, bicycloheptyl, etc..

Five- or six-membered heterocyclic radicals $R_9$, or as subtituents of alkyl radicals $R_4$, $R_6$ and $R_8$, can contain 1 or 2 hetero atoms, particularly nitrogen and/or oxygen. Heterocyclic ring systems containing the Si atom, which are formed by two of the radicals $R_4$, $R_6$ and $R_8$, including the type —$COR_9$, can be saturated or unsaturated; the hydrocarbon bridge is therefore alkylene or alkenylene.

Anions of di- and tri-alkylammonio radicals (which can be considered as salt forms of a dialkylamino radical) to be mentioned are, in particular, those of hydrohalic acids, alkylsulphonic acids and alkylphosphoric acids.

Preferred products of hydrolysis (hydrolysates) are those formed from monomers in which X represents chlorine or bromine, A represents a radical —$OR_4$, chlorine or methyl, B a radical —$OR_6$ or chlorine, and C a radical —$OR_8$ or chlorine, and which have a degree of polymerisation of 1, corresponding therefore to a dimer.

The polymerisation of β-halogenoethyl-silanes of formula I, initiated by hydrolysis, leads to structures which can be composed of linear-polymeric, cyclic-polymeric or cross-linked elements.

In the preferred cases, the β-halogenoethylsilyl-oxy-grouping can be denoted as common structural element, in which the original radicals A, B or C are partially contained, such as, e.g.

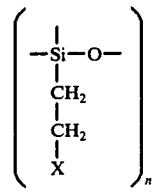

n is the "degree of polymerisation", n = 0 corresponds to the monomer starting material, n = 1 represents a dimer, n = 2 a trimer, etc.. The molecular weights of the preferred dimers are in the order of magnitude of 600 to 800.

The β-halogenoethylsilane hydrolysis and polymerisation products of β-halogenoethyl-silanes of formula I according to the invention affect, as well as their monomeric β-halogenoethyl-silane starting materials, in a varying manner the growth of parts of plants above and below the surface of the soil, and in the usually applied concentrations have a low toxicity towards warm-blooded animals. In these concentrations, the active substances cause moreover no morphological changes or damage which would result in the withering of the plant. The compounds are not mutagenic. Their action differs from that of a herbicidal active substance and of a fertiliser. The action corresponds more to the effects which can be observed on application of ethylene to various parts of plants. It is known that the plant itself produces, in the different stages of development, ethylene to a varying degree, particularly before and during the ripening process of the fruits, and at the end of the vegetation period with the occurring abscission of fruit and leaves. Since the regulation of ripening and of fruit and leaf abscission by application of chemical substances is of the greatest commercial importance in the cultivation of fruit, citrus fruit, pineapples and cotton, efforts have been made to favourably influence the development of the plant by external application of agents releasing ethylene. Thus, various classes of substances have meanwhile become known with which it has been possible to obtain certain such effects.

Such known compounds are relatively unstable under certain weather conditions, because under these particular conditions they are sensitive to hydrolysis. In the German 'Offenlegungsschrift' No. 2,149,680, β-halogenoethyl-silanes are described as active substances regulating plant growth. These compounds decompose in and on the plant with the release of ethylene, and are therefore similar in their mode and range of action to ethylene. Their slight but nevertheless noticeable hydrolysis-sensitivity necessitates special precautionary measures being taken, however, when these active-substance concentrates are stored in damp climatic zones.

Further compounds known as herbicidal active substances are halogenoalkyl-methyl-silanes [cp. US-Patent Nos. 3,390,976 and 3,390,977, and J. K. Leasure et al., J.Med.Chem. 9, 949 (1966)]. β-Chloroethyl (methyldimethoxy)silane was prepared by J. K. Leasure et al. (loc.cit), but has no herbicidal action.

The US-Pat. No. 3,183,076 describes α-chloroethyl-methyl-dialkoxy-silanes, which can be employed for the promotion of germination power, leaf abscission, etc., The present invention relates to new agents containing as active substances products obtained from the hydrolysis and polymerisation of β-halogenoethyl-silanes, which agents have a stimulating or retarding action on plant growth in the various stages of devolopment of the plant.

These storage-stable products of the hydrolysis and polymerisation of β-halogenoethyl-silanes of formula I are, by virtue of their dimeric or oligomeric structure, appreciably less sensitive to weather effects and to moisture, without them being noticeably any less effective. In addition to agents such as the usual carriers, distributing agents and light- and oxidation-stabilisers, the new products contain no agents combining with water, and consequently have an unlimited field of application.

The new agents influence the physiological processes of the plant development, and can be used for various purposes connected with the increase of yields, the facilitation of harvesting and the economy of labour in the handling of crops. The varied effects of these active substances depend greatly on the time of application with regard to the stage of development of the seed or of the plant, as well as on the applied concentrations.

By suitable treatment with the compounds according to the invention, it is possible to accelerate the ripening process of plants, and thus to obtain a better and more uniform ripening of fruits or of other crops, factors which in the case of various varieties of fruit, pineapples, tomatoes and tobacco and also other crops are of great commercial importance.

It has been found that products from the hydrolysis and polymerisation of compounds of formula I are excellently suitable for the regulation of the fall of fruit (fruit abscission). The harvesting of fruits such as, for example, olives, citrus fruits, cherries, apples, damsons, nuts and berries (currants, grapes, gooseberries, bilberries, cranberries, etc.) is conventionally done by hand.

In the course of growing rationalisation in agriculture, other methods for the harvesting of fruit have been promoted, and many different types of mechanical equipment developed for the purpose. As a rule, however, such mechanical devices damage the plants and the crops. It has been shown that fruit can be detached either without any mechanical assistance or with only a slight amount if the trees, bushes or plants are treated before the ripening of the fruit with the active substances according to the invention, with the result that harvesting is carried out more economically.

The promotion of abscission can also serve to obtain, by an early application of the active substances, a chemical thinning of the young fruits, an effect that is desirable in the case where the natural fruit set is too great, such as frequently occurs, for example, with apples, peaches or citrus fruits.

The vegetative plant growth and germination power are influenced by the new agents; and the blossom formation, the development of the fruit and the growth of abscission layers promoted. There is moreover a strengthening of the support tissues of the stalks of the treated plants. The formation of undesirable side shoots is very greatly reduced on various varieties of plants, such as in the case of tobacco and azalea; the vegetative growth on grape vines is likewise reduced. The new compounds also have a secretion-promoting action, e.g. the latex discharge is promoted in the case of Hevea brasiliensis, an effect of great commercial value. And tests have shown that the rooting of seedlings and cuttings is promoted. In addition, there occurs a simultaneous sprouting of dormant rhizomes, a factor which is particularly important in the case of various perennial weeds, such as couchgrass, Johnson grass and cyperus, which can then be easily destroyed or suppressed by herbicides. The germination capacity of seeds is promoted with low concentration levels and eliminated with higher ones. Both these effects are significant commercially. A control of the blossoming time and of the number of blossoms is possible in the case of many ornamental and cultivated plants. This effect is an especially important factor in the cultivation of pineapples. If all the trees or shrubs blossom simultaneously, then the crops can be gathered within a comparatively short space of time. With regard to cucurbitaceae and other plants, there occurs a displacement of the blossom sex differentiation in favour of pistillate flowers. The regulation of the blossom sex differentiation can be effectively used in practice, e.g. as an expedient for hybridising in seed growing, or for obtaining increases in yield, e.g. in the case of cucurbitaceae.

By regulation of blossom formation, blossom sex and vegetative growth, the active substances used according to the invention can appreciably increase the crop yield of plants (e.g. fruits, seeds, leaves).

The growth of shoots and roots can be regulated by the active substances in a manner depending on the concentration applied. It is thus possible to inhibit the growth of plants. Of commercial importance in this case is, for example, the retarding of the growth of grass along the edges of streets and paths or on lawns, since the frequency of cutting can thus be reduced.

Seed germination, sprouting of buds and rhizomes as well as growth of side shoots can be promoted or inhibited by the mentioned active substances, depending on the applied concentration. Thus, the seed germination and the sprouting of dormant rhizomes can be promoted in the case of weeds, effects which facilitate the destruction of these weeds by herbicides. On the other hand, the undesirable formation of side shoots on cut tobacco plants can be prevented.

Also to be emphasised is the possibility of using the substances according to the invention to initiate on certain plants the fall of leaves. The harvesting of cotton plants is thus rendered appreciably easier after the cotton plants have been defoliated by means of the said compounds. In the case of plants that are to be transplanted, transpiration can be reduced by defoliation.

Tests have also shown that a thinning of blossom and fruit occurs on fruit trees. Furthermore, there is obtained, e.g. with oranges, melons, apricots, peaches, tomatoes, bananas, bilberries, figs, coffee, pepper and pineapples, an acceleration and improvement of fruit ripening and colouration. And likewise the ripening of tobacco leaves is accelerated and improved. As a result of the development of abscission layers, the detachment of fruit and leaves is made appreciably more easy. This factor is of great importance in mechanical harvesting, e.g of citrus fruits, such as oranges, grapefruit, olives or stone fruit such as cherries, damsons, peaches, plums and apricots, or pomaceous fruit such as apples and pears, or soft fruit such as currants, rasberries and bilberries, or nuts such as walnuts and pecan nuts, or subtropical fruits such as coffee, figs and pepper. By suitable application of the above mentioned substances to certain crops such as cotton, French beans, green peas or ornamental shrubs, as well as to young plants, it is possible to produce defoliation, which likewise is of great commercial importance.

The extent and nature of the action are dependent on a wide variety of factors, particularly on the time of application with regard to the stage of development of the plant, and on the applied concentration. These factors vary, however, depending on the variety of plant and on the effect desired. Thus, for example, lawns are treated during the entire growth period; ornamental plants, of which, e.g. the intensity and number of the blossoms are to be increased, before development of the blossom setting; plants of which the fruit is to be sold, or in some other way utilised, at an appropriate interval of time before harvesting. Application of the active substances is effected by the use of solid or liquid agents, these being applied to parts of plants above the ground, to the surface of the soil, and into the soil. The preferred method is an application to the parts of the plants above the soil, for which purpose solutions or aqueous suspensions are most suitable. In addition to solutions and dispersions for the treatment of the growth substrate (soil), dusts, granulates and scattering agents are also suitable.

The essential promotion of the abscission of citrus fruits and bean leaves with the use of agents according to the invention has been demonstrated by the following tests:

The active substances are sprayed, in the form of solutions in a concentration of 0.2% and 0.4%, onto branches, well hung with fruit, of various orange trees. The tests are evaluated after 14 days according to the method developed by W. C. Wilson and C. H. Hendershott, [Proc. Am. Soc. Hort. Sc. 90, 123–129 (1967)]. The test consists of measuring the force in kg. required to detach the fruit.

The exact test procedure is as follows:

The agent is sprayed, in the form of solutions having a concentration of active substance of 0.4% and 0.2%, onto branches each carrying at least 15 to 20 ripe oranges. Seven days after application, the plucking force required to detach each of 10 similarly treated oranges is determined by means of a spring balance, and the average value from the 10 results recorded.

In the case of bean-leaf-abscission tests, segments of bean leaves of the variety "Tempo" are immersed with the petiole in a solution of 0.002% of active substance; eight segments per active substance are left in the solution of active substance for 6 days under controlled conditions. On specific days after commencement of the treatment, a count is made of the occurred abscissions (necking of the stalk on the leaf-side of the abscission zone).

Tests with agents containing the following active substances gave excellent results in that, after six days, all eight leaf segments had become detached from the petiole, and that the plucking force values for the oranges had decreased to below half the initial values.

product of hydrolysis of 2-chloroethyl-(methyl-dibenzoxy)-silane, product of hydrolysis of 2-chloroethyl-(tri-4'-methoxybenzoxy)-silane, product of hydrolysis of 2-chloroethyl-(tri-2'-methoxyethoxy)-silane, product of hydrolysis of 2-chloroethyl-(tri-acetoxy)-silane, product of hydrolysis of 2-bromoethyl-(tribenzoxy)-silane, product of hydrolysis of 2-chloroethyl-trichloro-silane, product of hydrolysis of 2-chloroethyl-(chloro-diethoxyethoxy)-silane.

All the products of hydrolysis and polymerisation of the β-halogenoethyl-silanes embraced by formula I are new substances. The new β-halogenoethylsilane hydrolysates and polymerisates are prepared according to the invention by a process in which a β-halogenoethylsilane of formula I

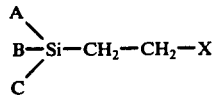

(I)

is allowed to react with water or with aqueous media.

During hydrolysis at least one bond that is not a Si-C bond splits, and the formed monomeric products combine, with the elimination of water, to form dimeric, oligomeric and, finally, polymeric molecular aggregates.

With a specific mean degree of polymerisation, the inclination for further polymerisation to occur gradually ceases, so that polymerisation to higher molecular products, even with the further presence of water, comes to a standstill; the products thus obtained are absolutely storage-stable products. Since on the other hand, however, the effect with higher degrees of polymerisation greatly decreases, hydrolysis has to be terminated at the latest after the formation of tetramers ($n = 3$), but preferably already after the formation of dimers.

The degree of polymerisation at which further polymerisation ceases is with a mean molecular weight of 1000 to 2000, and can attain a maximum of ca. 3000. The mean molecular weight of the preferred hydrolysate should not exceed 800.

The time taken for the maximum degree of polymerisation to be attained depends naturaly to a great extent on the temperature and on the reaction medium. Since the attainment of a high degree of polymerisation is not desired, there will in general be no addition made of hydrolysis accelerators such as acids, and, optionally, of solvents. Such additions are naturally applicable in the case of hydrolysis of short duration.

Alcohols, carboxylic acids, etc. can be added to the reaction medium, whereby, with the use of halogenoethyl-silanes in which at least one of the symbols A, B, C denotes chlorine, the polymerisation induced by hydrolysis is directed along paths where also parts of the molecules of these additives, such as alcohol or carboxylic acid radicals, are incorporated into the polymerised final product.

Hydrolysis can even be performed in moist air. But liquid aqueous media are preferred. Hydrolysis can be performed in the presence of solvents and/or diluents which are inert to the reactants. Particularly suitable as solubility-promoting agents are aprotic solvents such as, for example, aliphatic and aromatic hydrocarbons, e.g. hexane, cyclohexane, benzene, toluene, xylene, halogenated hydrocarbons such as chlorinated ethylene, carbon tetrachloride, chloroform, chlorobenzene, and also ethers and ethereal compounds such as diethyl ether, tetrahydrofuran, etc.

It can moreover be necessary in some cases to add to the reaction mixture equivalent or catalytic amounts of acids, such as, e.g. hydrochloric acid, sulphuric acid or acetic acid.

The hydrolysis temperatures are in the range of 0° to 100° C; the duration of the reaction can be between a few minutes and several days.

The starting materials of formula I wherein two of the symbols A, B or C represent phenyl or lower alkyl having 2 to 6 carbon atoms, the third represents chlorine, and X chlorine or bromine, or wherein at least one of the symbols A, B or C represents phenyl or lower alkyl having 2 to 6 carbon atoms, and X denotes bromine, have not been hitherto described in the literature. They are produced by methods known per se, e.g. by HBr addition to the corresponding vinylsilanes of formula VIII, analogously to a mode of reaction described by A. I. Bourne (J. Chem. Soc. sect. C, 1970, 1740):

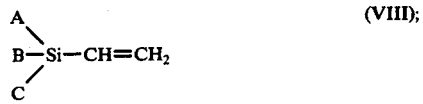

or by the reaction of ethylsilanes of formula IX

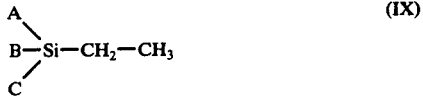

with chlorine, wherein one of the symbols A, B or C represent lower alkyl having 2 to 6 carbon atoms [cp. J. K. Leasure et al, J. Med. Chem. 2, 949 (1966)]; or by the reaction of β-halogenoethyl-trichlorosilane of the formula

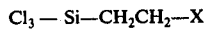

with one, two or three equivalents of a Grignard compound Alkyl-Mg-X or phenyl-Mg-X in which X denotes chlorine or bromine [cp. A. D. Petrov et al., Izvest. Akad. Nauk S.S.S.R., Otdel. Khim. Nauk 1957, 310].

The remaining starting materials of formula I are known, or can be prepared, e.g. by reaction of β-halogenoethyl-trichlorosilane, β-halogenoethylmethyl-dichlorosilane or β-halogenoethyl-dimethylchlorosilane, β-chloroethyl-phenyldichlorosilane with alcohols, carboxylic acids, carboxylic acid anhydrides, mercaptans or amines, corresponding to the data contained in the German 'Offenlegungsschrift' No. 2149680, and in the Swiss patent application Nos. 11943/71, 3048/72 and 4733/72; or by reaction of vinylsilanes with hydrohalic acids.

The following examples serve to illustrate the hydrolysis process according to the invention. In the attached tables are given the products of hydrolysis prepared according to the examples, as well as other such products obtained in the manner described in the examples, together with the respective starting products. Temperatures are expressed in degrees Centigrade, and pressures in Torr.

EXAMPLE 1

15.8 g of 2-chloroethyl-tris(2'-methoxy)-silane is dissolved in 5 ml of 2-methoxyethanol; to this solution there is then added a mixture of 0.8 g of water and 0.1 g of 0.5N aqueous hydrochloric acid. The reaction mixture is subsequently allowed to stand for 3 days in a closed container at room temperature. The mixture is afterwards concentrated for one hour at room temperature under 14 Torr, for two hours at room temperature under 0.1 Torr and for two hours at 40° under 0.001 Torr to obtain 8.75 g of an oil, $n_D^{20} = 1.4559$. The mean molecular weight of the oil thus obtained is 606.

The mean molecular weights of the polymers in the examples were determined by the vapour-pressure osmosis method.

EXAMPLE 2

23.5 g of 2-bromoethyl-(methyl-di-2-butenyloxy)-silane is dissolved in 40 ml of acetone, and a mixture of 5.2 g of water and 0.6 g of 0.5N aqueous hydrochloric acid added to the solution. The reaction conditions and processing methods applied are analogous to those in Example 1. The yield is 15 g of an oil, $n_D^{20} = 1.4910$. The mean molecular weight of the resulting oil is 725.

EXAMPLE 3

19.8 g of 2-chloroethyl-(trichloro)-silane is dissolved in 50 ml of diethyl ether, and an addition then made at −25° to −20° in the course of 45 minutes of 27.6 g of 2-phenoxyethanol. The reaction mixture is allowed to warm up within 30 minutes to 0°; at this temperature there is then added dropwise 0.9 g of water within 15 minutes, and stirring maintained for a further 12 hours at room temperature. Diethyl ether is evaporated off in vacuo, and the residue dried for 2 hours under 0.001 Torr. The resulting yield is 36 g of a colourless oil, $n_D^{20} = 1.5425$. The mean molecular weight is 681.

EXAMPLE 4

37.2 g of 2-chloroethyl-(metyl-dichloro)-silane is dissolved in 200 ml of diethyl ether; an addition is then made at 0° in the course of 3 minutes of 15.25 g of benzyl alcohol and 2.52 g of water dissolved in 20 ml of acetone. The subsequent reaction conditions and processing methods correspond to those in Example 3.

There is thus obtained 36.5 g of a viscous oil, $n_D^{22} = 1.5045$.

EXAMPLES 5

19.0 g of 2-chloroethyl-tris(octylamino)-silane is dissolved in 100 ml of diethyl ether, and 2.88 g of water dissolved in 19.2 g of glacial acetic acid added at −10° to −5° within 15 minutes; stirring is then maintained for one hour at −10° and for 18 hours at room temperature. The reaction mixture is concentrated in vacuo, and an addition subsequently made of 300 ml of petroleum ether. The whole is filtered and concentrated in vacuo; further petroleum ether (200 ml) is added to the oily residue; filtration is repeated and the filtrate again concentrated in vacuo. The residue is dried for 3 hours at 40°/0.001 Torr to obtain 19.0 g of a viscous oil, $n_D^{20} = 1.4385$.

EXAMPLES OF PROCEDURES FOR THE PREPARATION OF STARTING MATERIALS a. 88.2 g of triethylchlorosilane, 50 g of sulphuryl chloride and 0.4 g of dibenzoylperoxide are stirred together under refluxing conditions for 4 hours. After fractional distillation, the resulting yield is 20 g of 2-chloroethyl-(diethyl-chloro)-silane; B.P. 135°-137°/100 Torr.

b. 40.6 g of phenylvinyldichlorosilane is placed into a vessel, and at 20° to 25° hydrogen bromide introduced with UV-irradiation. After completed reaction (ca. 70 minutes), the excess HBr is blown out with dry nitrogen. The resulting yield is 52 g of 2-bromoethyl(-phenyl)-dichloro)-silane, B.P. 105°/0.1 Torr

|    | Calculated: | Found: |
|----|-------------|--------|
| C  | 33.8        | 33.9   |
| H  | 3.2         | 3.1    |
| Br | 28.2        | 28.4   |
| Cl | 24.9        | 24.1   |
| Si | 9.9         | 10.2   | c. 9.9 g of 2-bromoethyl-(phenyl-dichloro)-silane is dissolved in 100 ml of absolute diethyl ether, and an addition made at −15° to −10° within 5 minutes of a mixture of 7.6 g of benzyl alcohol and 5.5 g of absolute pyridine dissolved in 25 ml of absolute ether. The reaction mixture is allowed to warm up within one hour to room temperature, and stirring is maintained for 4 hours at the reflux temperature. The reaction mixture is filtered, and the filtrate concentrated in vacuo to obtain 14.9 g of 2-bromoethyl(phenyl-dibenzyloxy)-silane, $n_D^{20} = 1.5748$.

|    | Calculated: | Found: |
|----|-------------|--------|
| C  | 61.8        | 61.8   |
| H  | 5.4         | 5.4    |
| Br | 18.7        | 18.6   |
| Si | 6.6         | 6.7    |

Polymerisation products obtained from hydrolysis of ββof formula I are given in Table I.

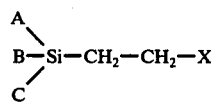

Table 1

| No. | A | B | C | X | Mol amounts water/silane/alcohol | | | Physical data MM=mean molecular weight |
|---|---|---|---|---|---|---|---|---|
| 1 | Methyloxy | =A | A | Cl | 8 | 1 | 0 | $n_D^{20}=1,4862$ |
| 2 | 2-Methoxyethoxy | " | " | " | 1 | 1 | 0 | $n_D^{20}=1,4559$ |
| 3 | " | " | " | " | 2 | 1 | 0 | $n_D^{20}=1,4755$ MM=1400 |
| 4 | " | " | " | " | 4 | 1 | 0 | $n_D^{20}=1,4823$ |
| 5 | " | " | " | " | 8 | 1 | 0 | $n_D^{20}=1,4816$ |
| 6 | " | " | " | " | 16 | 1 | 0 | $n_D^{23}=1,4858$ MM=1350 |
| 7 | 4-Methoxybenzoxy | " | " | " | 4 | 1 | 0 | $n_D^{22}=1,5463$ |
| 8 | " | " | " | " | 1 | 2 | 0 | $n_D^{20}=1,5545$ |
| 9 | Phenyloxy | " | " | " | 4 | 1 | 0 | $n_D^{20}=1,5207$ |
| 10 | 2-Phenoxyethoxy | " | " | " | 8 | 1 | 0 | $n_D^{20}=1,5320$ |
| 11 | Benzyloxy | " | " | Br | 2 | 1 | 0 | $n_D^{20}=1,5400$ |
| 12 | Octylamino | " | " | Cl | 4 | 1 | 0 | $n_D^{20}=1,4385$ |
| 13 | Acetyloxy | " | " | " | 8 | 1 | 0 | $n_D^{26}=1,4960$ MM=3100 |
| 14 | Octyloxy | " | $CH_3$ | Br | 16 | 1 | 0 | $n_D^{20}=1,4445$ |
| 15 | 2-Butenyloxy | " | " | " | 4 | 1 | 0 | $n_D^{20}=1,4910$ MM=725 |
| 16 | 3-Hexinyloxy | " | " | Cl | 4 | 1 | 0 | $n_D^{20}=1,4715$ |
| 17 | Benzyloxy | " | " | " | 8 | 1 | 0 | $n_D^{20}=1,5180$ |
| 18 | Chlorine | " | " | " | 1 | 2 | 2(Tetrahydrofurfuryl alcohol) | $n_D^{20}=1,4715$ MM=386 |
| 19 | " | " | " | " | 2 | 3 | 2(Benzyl alcohol) | $n_D^{22}=1,5045$ MM=440 |
| 20 | " | " | " | " | 3 | 4 | 0 | $n_D^{20}=1,4719$ MM=521 |
| 21 | " | " | A | " | 3,2 | 3,4 | 3,8(2-Methoxy)ethanol | MM=976 |
| 22 | " | " | " | " | 1 | 2 | 4(Methanol) | MM=464 |
| 23 | Benzyloxy | " | Cl | " | 4 | 1 | 0 | $n_D^{22}=1,5168$ MM=1040 |
| 24 | 2-Ethoxyethoxy | " | " | " | 1 | 2 | 0 | $n_D^{20}=1,4611$ MM=1100 |
| 25 | Hexyloxy | $CH_3$ | $CH_3$ | Br | 2 | 1 | 0 | $n_D^{20}=1,4409$ |
| 26 | Benzyloxy | Butyl mercapto | " | Cl | 4 | 1 | 0 | $n_D^{20}=1,4935$ |
| 27 | Chlorine | =A | =A | " | 1 | 2 | 4(Butanol) | $n_D^{20}=1,4410$ MM=479 |
| 28 | " | " | " | Br | 1 | 2 | 4(2-Butenol) | $n_D^{20}=1,4835$ MM=647 |
| 29 | " | " | " | Cl | 1 | 2 | 4(3-Phenylpropanol) | $n_D^{20}=1,5317$ MM=655 |
| 30 | " | " | " | " | 1 | 2 | 4(2-Ethylthioethanol) | $n_D^{20}=1,5052$ MM=736 |
| 31 | " | " | " | " | 1 | 2 | 4(2-Phenoxyethanol) | $n_D^{20}=1,5425$ MM=736 |
| 32 | " | " | " | " | 1 | 2 | 4(4-Methylbenzyl alcohol) | $n_D^{20}=1.5384$ |
| 33 | " | " | $CH_3$ | " | 1 | 2 | 2 " | $n_D^{20}=1,5150$ MM=386 |
| 34 | " | " | " | Br | 1 | 2 | 2(Methanol) | $n_D^{20}=1,4875$ MM=488 |

| No. | A | B | C | X | Mol amounts water/silane/dimethyldichlorosilane | | | Physical data MM=mean molecular weight |
|---|---|---|---|---|---|---|---|---|
| 35 | Chlorine | Chlorine | Methyl | Cl | 4 | 1 | 2 | MM=1300 |
| 36 | " | " | " | Br | 4 | 1 | 2 | MM=1250 |

β-Halogenoethyl-silanes (starting materials) of formula I are listed in Table II:

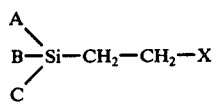

Table II

| No. | A | B | C | X | Physical data |
|---|---|---|---|---|---|
| 37 | Ethyl | Ethyl | Chlorine | Cl | B. P. = 135–139°/100 Torr |
| 38 | Phenyl | Phenyl | " | Br | |
| 39 | " | Chlorine | " | " | B. P. = 105°/0,1 Torr |
| 40 | " | Acetyloxy | =B | " | $n_D^{20} = 1,5315$ |
| 41 | " | Benzyloxy | " | " | $n_D^{20} = 1,5748$ |
| 42 | " | 2-Butenyloxy | " | " | $n_D^{20} = 1,5202$ |
| 43 | " | Methyloxy | " | " | $n_D^{20} = 1,5195$ |
| 44 | " | 4-Methylbenzyloxy | " | " | $n_D^{20} = 1,5671$ |
| 45 | " | 4-Methoxybenzyloxy | " | " | $n_D^{20} = 1,5730$ |
| 46 | " | 2-Methoxyethoxy | " | " | $n_D^{20} = 1,5079$ |
| 47 | " | Octyloxy | " | " | $n_D^{20} = 1,4915$ |
| 48 | " | 2-Phenoxyethyl | " | " | $n_D^{20} = 1,5640$ |
| 49 | " | 2-Propinyloxy | " | " | $n_D^{20} = 1,5414$ |
| 50 | " | Octadecyloxy | " | " | $n_D^{28} = 1,4810$ |
| 51 | " | Butylmercapto | " | " | |
| 52 | " | Benzylmercapto | " | " | |
| 53 | " | Phenylamino | " | " | |

Agents according to the invention are prepared in a manner known per se by the intimate mixing and grinding of polymerisation products of β-halogenoethyl-silanes of the general formula I, formed by hydrolysis, with suitable carriers, optionally with the addition of dispersing agents or solvents that are inert to the active substances.

Water-dispersible concentrates of active substance, i.e. wettable powders, pastes and emulsion concentrates, are active-substance concentrates which can be diluted with water to obtain any desired concentration. They consist of active substance, carrier, optionally additives stabilising the active substance, surface-active substances and anti-foaming agents and, optionally, solvents. The concentration of active substance in these agents is 0.5 – 80%.

The wettable powders and pastes are obtained by the mixing and grinding of the active substances with dispersing agents and pulverulent carriers, in suitable devices, until homogeneity is attained. Suitable carriers are, e.g. the following:

kaolin, talcum, loess, chalk, limestone, ground limestone, bole, Attaclay, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate ammonium nitrate, urea, ground vegetable products such as bran, bark dust, sawdust, ground nutshells, cellulose powder, residues of plant extractions, active charcoal, transalone or in admixture with each other.

Suitable dispersing agents are, e.g. the following:

condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylarylsulphonates, alkali metal salts and alkaline-earth metal salts of dibutylnaphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkali-metal and alkaline-earth metal salts To these mixtures may also be added additives stabilising the active substance, and/or non-ionic, anion-active and cation-active substances, which, for example, improve the adhesiveness of the active substances on plants and on parts of plants (adhesives and agglutinans), and/or ensure a better wettability (wetting agents). Suitable adhesives are, for example, the following:

olein/lime mixture, ce.llulose derivatives (methyl cellulose, carboxymethyl cellulose), hydroxyethylene glycol ethers of mono- and dialkylphenols having 5 – 15 ethylene oxide radicals per molecule and 8 – 9 carbon atoms in the alkyl radical, ligninsulphonic acid, alkali metal and alkaline-earth metal salts thereof, polyethylene glycol ethers (carbowaves), fatty alcohol polyglycol ethers having 5 – 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea/formaldehyde, as well as latex products. The active substances are so mixed, ground, sieved and strained with the above mentioned additives that the solid constituent in the case of wettable powders has a particle size not exceeding 0.02 to 0.04 mm, and in the case of pastes not exceeding 0.03 mm.

Emulsion concentrates and pastes are prepared by application of the dispersing agents such as those mentioned in the preceding paragraphs, organic solvents and water. Suitable solvents are, e.g. the following:

ketones benzene, xylenes, toluene, dimethylsulphoxide, and mineral oil fractions boiling in the range of 120° to 350°. The solvents must be practically odourless, non-phytotoxic, and inert to the active substances.

Furthermore, the agents according to the invention can be employed in the form of solutions. For this purpose, the active substance (or several active substances) if the general formula I is (or are) dissolved in suitable organic solvents, solvent mixtures, or water. The following can be used as organic solvents: aliphatic and aromatic hydrocarbons, chlorinated derivatives thereof, alkylnaphthalenes or mineral oils on their own or in admixture with each other. The solutions should contain the active substances in a concentration range of from 1 to 20%.

The solid preparations, such as dusts, scattering agents and granulates, contain solid carriers, such as those mentioned in the foregoing, and, optionally, additives stablising the active substance. The particle size of the carriers is for dusts advantageously up to about 0.1 mm; for scattering agents from about 0.075 mm to 0.2 mm; and for granulates 0.2 mm or coarser. the concentrations of active substance in the solid preparations are from 0.5 to 80%.

All the mentioned active substances concentrates may also contain agents stabilising against the effects of light, and antioxidants. Furthermore, other growth-regulating substances can be mixed with the active substances, which are able, if necessary, to intensify the biological activity of the products of hydrolysis of the $\beta$-halogenoethyl-silanes, or facilitate selectivity with respect to the time and mode of action of the agents applied.

GRANULATE

The following substances are used for the preparation of a 5% granulate:

| | |
|---|---|
| 5 | parts of 2-chloroethyl-(methyl-dibenzoxy)-silane-hydrolysate, |
| 0.25 | parts of epichlorohydrin, |
| 0.25 | parts of cetyl polyglycol ether, |
| 3.50 | parts of polyethylene glycol ("carbowax"), |
| 91 | parts of kaolin (particle size 0.2 – 0.8 mm). |

The active substance is mixed with epichlorohydrin and the mixture dissolved in 6 parts of acetone; to the solution are then added polyethylene glycol and cetyl polyglycol ether. The thus obtained solution is sprayed on to kaolin, and the acetone subsequently evaporated in vacuo.

WETTABLE POWDER

The following constituents are used for the preparation of (a) a 40%, (b) a 50%, (c) a 25%, and (d) a 10% wettable powder:

| | | |
|---|---|---|
| a) | 40 | parts of 2-chloroethyl-(di-4'-methoxybenzoxy)-silane-hydrolysate, |
| | 5 | parts of sodium lignin sulphonate, |
| | 1 | part of sodium dibutyl-naphthalene sulphonate, |
| | 54 | parts of silicic acid; |
| b) | 50 | parts of 2-chloroethyl-(tri-2'-methoxyethoxy)-silane-hydrolysate, |
| | 5 | parts of alkylaryl sulphonate ("Tinovetin B"), |
| | 10 | parts of calcium lignin sulphonate, |
| | 1 | part of Champagne chalk/hydroxyethyl cellulose mixture (1 : 1), |
| | 20 | parts of silicic acid, |
| | 14 | parts of kaolin; |
| c) | 25 | parts of 2-chloroethyl-(tri-acetoxy)-silane-hydrolysate, |
| | 5 | parts of the sodium salt of oleylmethyl tauride, |
| | 2.5 | parts of naphthalenesulphonic acid/formaldehyde condensate, |
| | 0.5 | parts of carboxymethyl cellulose, |
| | 5 | parts of neutral potassium aluminium silicate, |
| | 62 | parts of kaolin; |
| d) | 10 | parts of 2-bromoethyl-(tribenzoxy)-silane hydrolysate, |
| | 3 | parts of a mixture of the sodium salts of saturated fatty alcohol sulphates, |
| | 5 | parts of naphthalenesulphonic acid/formaldehyde condensate |
| | 82 | parts of kaolin. |

The active substances are intimately mixed, in suitable mixers, with the additives; the mixture is subsequently ground in suitable mills and rollers. Wettable powders are thus obtained which can be diluted with water to give suspensions of any desired concentration. Such suspensions are employed, e.g. for the removal of undesired side shoots, for the tillering of lawns, and for the rooting of seedlings and cuttings, etc.

EMULSION CONCENTRATE

The following constituents are mixed together to produce 25% emulsion concentrates:

| a) | 25 parts of 2-chloroethyl-(di-4'-methoxybenzoxy)-silane hydrolysate, |
| --- | --- |
| | 5 parts of a mixture of nonylphenolpolyoxyethylene and calcium-dodecylbenzene sulphonate, |
| | 70 parts of xylene; |
| b) | 25 parts of 2-chloroethyl-(tri-2'-methoxyethoxy)-silane hydrolysate, |
| | 10 parts of a mixture of nonylphenolpolyoxyethylene and calcium-dodecylbenzene sulphonate, |
| | 65 parts of cyclohexanone. |

This concentrate can be diluted with water to obtain emulsions of any desired concentration. Such emulsions are suitable for the thinning out of blossom and fruit, for the accelerated ripening of fruits, and for the promotion of fruit and leaf abscission.

What we claim is:

1. Partially polymerised products from the hydrolysis of beta-halogenoethylsilanes, with a degree of polymerisation of at most 3, which are obtained by hydrolysis of beta-halogenoethyl-silanes of formula I

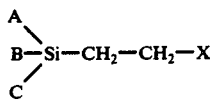

wherein
X represents chlorine or bromine,
A represents a radical —O—R$_4$, chlorine or the methyl group,
B represents a radical —O—R$_6$ or chlorine, and
C represents a radical —O—R$_8$ or chlorine, wherein the radicals
R$_4$, R$_6$ and R$_8$ each independently represent C$_1$–C$_{18}$ alkyl; C$_1$–C$_6$ alkyl substituted by halogen; C$_1$–C$_{18}$ alkyl substituted by C$_3$–C$_{12}$ cycloalkyl; C$_3$–C$_{18}$ alkenyl; C$_3$–C$_{12}$ cycloalkenyl; C$_3$–C$_{18}$ alkenyl; C$_3$–C$_8$ alkynyl or C$_3$–C$_{12}$ cycloalkyl substituted by phenyl or halogen; phenyl optionally mono- or polysubstituted by C$_1$–C$_8$ alkyl or C$_1$–C$_6$ halogenoalkyl; benzyl radicals optionally mono- or polysubstituted by C$_1$–C$_8$ alkyl or halogen.

2. Products of hydrolysis according to claim 1 which have a degree of polymerisation of 1, which is equivalent to a dimer.

3. Process for the preparation of partially polymerised products of the hydrolysis of β-halogenoethyl-silanes, in which process at least one β-halogenoethyl-silane of formula I of claim 1 is treated with water or with an aqueous medium until a polymerisation product having a degree of polymerisation of at most 3 (tetramer) is obtained.

4. Process according to claim 3, wherein the β-halogenoethyl silane used for polymerisation is one of formula I wherein at least two of the radicals A, B and C represent chlorine, and wherein, after reaction with $n-1$ equivalents of alcohols or carboxylic acids, relative to $n$ chlorine atoms bound to Si, the hydrolysis is performed with 1 equivalent of water, relative to the remaining chlorine atom.

5. Process according to claim 3, wherein a β-halogenoethyl-silane is subjected to hydrolysis, whereby in formula I
X represents chlorine or bromine,
A represents a radical —OR$_4$, chlorine or the methyl group,
B represents a radical —OR$_6$ or chlorine, and
C represents a radical —OR$_8$ or chlorine,
and the hydrolysis reaction is stopped before a polymer having a degree of polymerisation of 2 (trimer), or a mean molecular weight exceeding 800, has been formed.

6. The product of claim 1 which is obtained by the hydrolysis of 2-chloroethyl-(chloro-dimethoxy)silane.

7. The process of claim 4, wherein 2 moles of 2-chloroethyl-(trichloro)silane, 4 moles of methanol and 1 mole of water are reacted.

* * * * *